(12) United States Patent
Maltz

(10) Patent No.: US 7,898,192 B2
(45) Date of Patent: Mar. 1, 2011

(54) MODULAR LINAC AND SYSTEMS TO SUPPORT SAME

(75) Inventor: Jonathan S. Maltz, Oakland, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 912 days.

(21) Appl. No.: 11/810,783

(22) Filed: Jun. 6, 2007

(65) Prior Publication Data
US 2008/0303457 A1   Dec. 11, 2008

(51) Int. Cl.
*H05H 9/00*   (2006.01)
*A61N 5/10*   (2006.01)

(52) U.S. Cl. .......................... 315/505; 378/65

(58) Field of Classification Search ................ 315/500, 315/501, 502, 503, 504, 505; 378/62–65, 378/19, 137–138
See application file for complete search history.

(56) References Cited

U.S. PATENT DOCUMENTS

| | | | |
|---|---|---|---|
| 4,647,884 A | | 3/1987 | Lang et al. |
| 5,479,021 A | * | 12/1995 | Morgan et al. ......... 250/363.04 |
| 6,466,455 B2 | * | 10/2002 | Kirbie .......................... 363/16 |
| 6,493,424 B2 | * | 12/2002 | Whitham ..................... 378/137 |
| 6,529,387 B2 | * | 3/2003 | Kirbie .......................... 363/16 |
| 7,115,094 B2 | * | 10/2006 | Azuma et al. ............... 600/459 |
| 2008/0107239 A1 | * | 5/2008 | Sayeh et al. ................ 378/148 |

OTHER PUBLICATIONS

R.G. Schonberg et al., "Portable, X-Band, Linear Accelerator Systems", IEEE Transactions on Nuclear Science, vol. NS-32, No., Oct. 1985. pp. 3234-3236.
http://www.accuray.com/Products/Cyberkife/index.aspx, CyberKnife® System, 3 pages total, Accuray.

* cited by examiner

*Primary Examiner*—Douglas W Owens
*Assistant Examiner*—Minh D A

(57) ABSTRACT

Some embodiments include an accelerator waveguide to generate an accelerated radiation beam, and a housing to house to accelerator waveguide. The housing may include an interface to couple the housing to and to decouple the housing from a movable support. Some aspects include coupling a first interface of a housing to a first interface of a movable support, and uncoupling the first interface of the housing from the first interface of the movable support, wherein the housing includes an accelerator waveguide to generate an accelerated radiation beam.

13 Claims, 11 Drawing Sheets

MODULAR LINAC AND SYSTEMS TO SUPPORT SAME

BACKGROUND

1. Field

The embodiments described herein relate generally to linear accelerators. More particularly, the described embodiments relate to modular linear accelerators for selective mounting onto various movable supports.

2. Description

A linear accelerator produces electrons or photons having particular energies. In one common application, a linear accelerator produces a radiation beam used for medical radiation treatment. The beam may be directed toward a target volume of a patient in order to destroy cells within the target volume by causing ionizations within the cells or other radiation-induced cell damage.

Conventional linear accelerators may be used for isocentric or non-isocentric radiation treatment. Isocentric treatment is typically delivered by a linear accelerator integrated into a rotatable gantry. The gantry rotates around a horizontal axis such that a beam emitted from the linear accelerator passes through a same volume of space (i.e., an isocenter) at each angle of rotation. A target volume of a patient is therefore positioned at the isocenter prior to emission of the beam and rotation of the gantry. Due to physical constraints, isocentric treatment is particularly suited to target volumes located above the chest region.

Multi-jointed robotic arms are typically used to deliver non-isocentric radiation treatment. Such arms include an integrated linear accelerator and may be precisely positioned with respect to a patient in order to deliver treatment radiation to a target volume located virtually anywhere within the patient. Non-isocentric radiation treatment therefore irradiates the target volume from fewer external positions than those used during isocentric radiation treatment.

Isocentric and non-isocentric radiation treatments present characteristic advantages and shortcomings. Treatment facilities would prefer to offer either or both types of treatment depending on the nature of a particular patient and patient volume. However, the purchase, maintenance, and staffing costs associated with an isocentric radiation treatment machine and with a non-isocentric radiation treatment machine often prevent facilities from offering both types of treatment. Even if costs were not prohibitive, the relative size of each type of machine typically prohibits co-location of two of such machines in a same treatment vault, thereby further exacerbating the current inefficiencies of offering both types of treatment.

SUMMARY

In order to address the foregoing, some embodiments provide an accelerator waveguide to generate an accelerated radiation beam, and a housing to house to accelerator waveguide, the housing comprising an interface to couple the housing to and to decouple the housing from a movable support. An electron gun may be disposed within the housing, the electron gun to receive signals from the interface and to inject electrons into the accelerator waveguide based on the signals.

The movable support may include a gantry to rotate about a patient isocenter and a second interface to mate with the interface. According to some aspects, the movable support includes a multi-jointed robotic arm and a second interface to mate with the interface. The housing may include a second interface to couple the housing to and to decouple the housing from a second movable support.

Some embodiments provide a movable support comprising an interface to selectively receive and decouple a housing, wherein the interface is to provide signals to control an electron gun to the housing. In some aspects, the interface is to provide signals to control an accelerator waveguide to the housing, and the interface is to provide cooling fluid to the accelerator waveguide.

Still further aspects may include a method to couple a first interface of a housing to a first interface of a movable support, where the housing includes an accelerator waveguide to generate an accelerated radiation beam, and to uncouple the first interface of the housing from the first interface of the movable support. The first interface of the housing may then be coupled to a second interface of a second movable support. Further to this aspect, the movable support may comprise a rotatable gantry, and the second movable support may comprise a multi-jointed robotic arm.

In some aspects, first signals are provided from the first interface of the movable support to an electron gun disposed within the housing, the electron gun to inject electrons into the accelerator waveguide to generate a first radiation beam based on the first signals, a second interface of the housing is coupled to a second interface of a second movable support, and second signals are provided from the second interface of the second movable support to the electron gun, the electron gun to inject electrons into the accelerator waveguide to generate a second radiation beam based on the signals. The first radiation beam may be directed to a patient isocenter, and the second radiation beam may be directed at a patient volume other than the patient isocenter.

The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein.

DETAILED DESCRIPTION

The following description is provided to enable a person in the art to make and use some embodiments and sets forth the best mode contemplated by the inventor for carrying out some embodiments. Various modifications, however, will remain readily apparent to those in the art.

Figure 1:
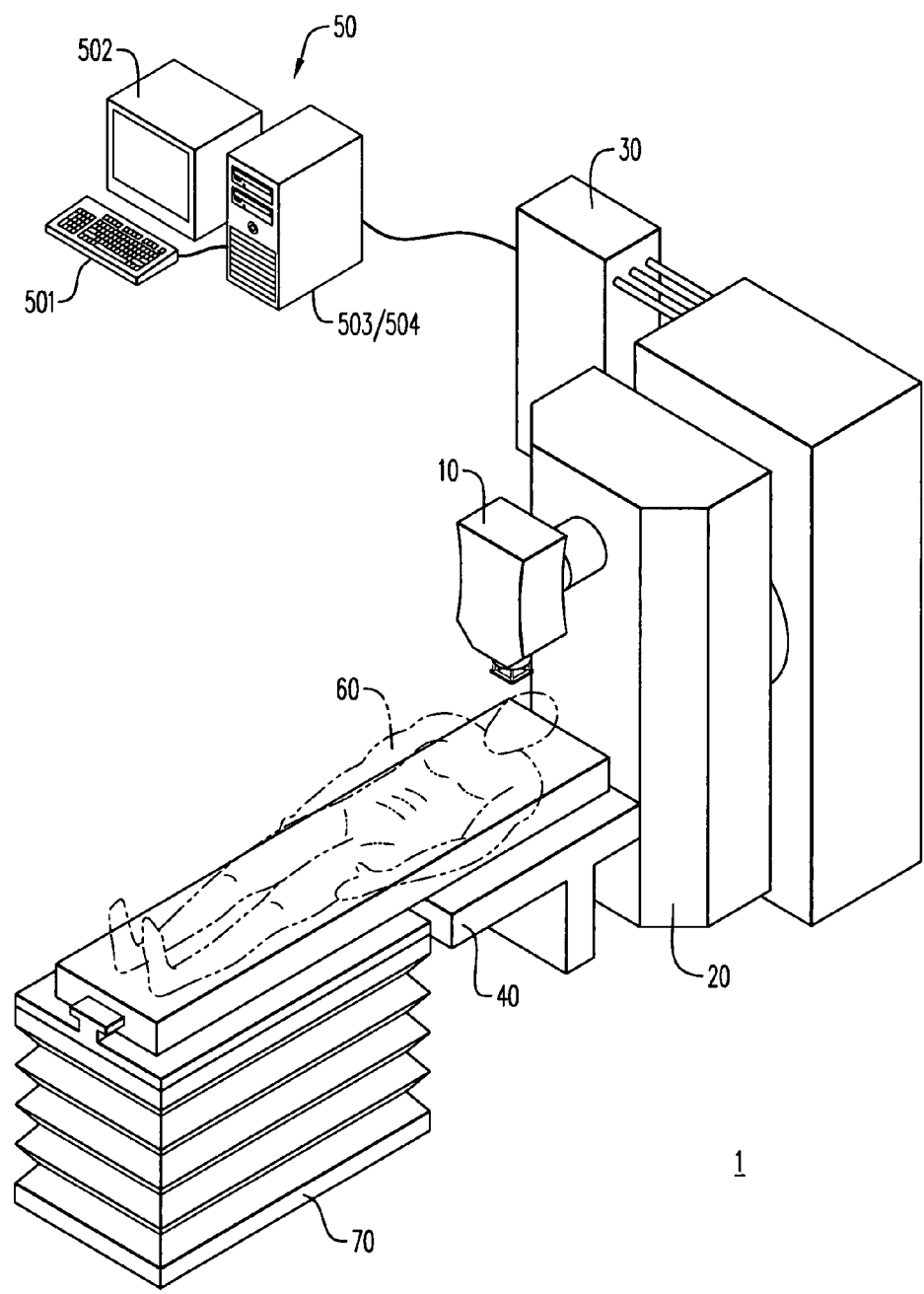
FIG. 1 is a perspective view of a treatment room according to some embodiments.

FIG. 1 is a perspective view of treatment room 1 according to some embodiments. Located within treatment room 1 are linear accelerator housing 10, rotatable gantry 20, power/RF unit 30, imaging device 40, operator console 50, beam object 60, and table 70. The elements of treatment room 1 may be used to deliver radiation treatment to a target volume of beam object 60. In this regard, beam object 60 comprises a patient positioned to receive radiation according to a radiation treatment plan. The elements of treatment room 1 may be employed in other applications according to some embodiments.

Linear accelerator housing 10 houses an accelerator waveguide to generate an accelerated radiation beam. The radiation beam may comprise photon radiation or electron radiation having various energies. According to some embodiments, housing 10 may deliver a radiation beam toward a volume of object 60 that is located at an isocenter of housing 10 and gantry 20. The isocenter is located at an intersection between an axis of rotation of gantry 20 and an axis of the emitted radiation beam. Various implementations of housing 10 according to some embodiments are described below.

In some embodiments, housing 10 includes an interface (not shown) to couple housing 10 to gantry 20 and to decouple housing 10 from gantry 20. Gantry 20 may therefore comprise a corresponding interface to facilitate this coupling/decoupling. The interfaces of housing 10 and gantry 20 may physically support housing 10 and/or pass DC power, RF pulses, RF power, control signals and/or cooling fluid between housing 10 and gantry 20.

Power/RF unit 30 provides inputs that may be required for operation of housing 10. Power/RF unit 30 may deliver these inputs to gantry 20 via one or more cables, conduits, waveguides, etc., and gantry 20 may pass the inputs onto housing 10 via its interface thereto. In some embodiments, one or more of the inputs are directly provided to housing 10 from power/RF unit 30.

Power/RF unit 30 may provide RF power and RF pulses used to generate an accelerated radiation beam, and cooling fluid for cooling elements of housing 10. Power/RF unit 30, as will be described below, may comprise several separate units. For example, power/RF unit 30 may comprise an RF unit to provide the aforementioned RF power and RF pulses and a separate power unit to provide high- and low-voltage power to the RF unit. These units may be located separate from each other and from gantry 20 in accordance with their operational constraints. For example, difficulty in transmitting RF signals may require placement of an RF unit within a few meters of gantry 20, while a power unit may be located tens of meters from gantry 20.

Imaging device 40 may comprise any system to acquire an image based on received photon radiation (i.e., X-rays) and/or electron radiation. Imaging device 40 acquires images that are used before, during and after radiation treatment. For example, imaging device 40 may be used to acquire images for diagnosis, verification and recordation of a patient position, and verification and recordation of an internal patient portal to which treatment radiation is delivered.

In some embodiments, imaging device 40 is a flat-panel imaging device using a scintillator layer and solid-state amorphous silicon photodiodes deployed in a two-dimensional array. In other embodiments, imaging device 40 converts X-rays to electrical charge directly using an array of amorphous selenium photoconductors. Imaging device 40 may also comprise a CCD or tube-based camera. Such an imaging device may include a light-proof housing within which are disposed a scintillator, a mirror, and a camera.

Imaging device 40 may be attached to gantry 20 in any manner, including via an extendible and retractable housing. As mentioned above, gantry 20 is rotatable around an axis before, during and after emission of a radiation beam by housing 10. Rotation of gantry 20 may cause housing 10 and imaging device 40 to rotate around the isocenter such that the isocenter remains located between housing 10 and imaging device 40 during the rotation.

Table 70 supports object 60 during radiation therapy. Table 70 may be adjustable to ensure, along with rotation of gantry 20, that a target volume is positioned between housing 10 and imaging device 40. Table 70 may also be used to support devices used for acquisition of correction images, other calibration tasks and/or beam verification.

Operator console 50 includes input device 501 for receiving instructions from an operator and output device 502, which may be a monitor for presenting operational parameters of linear accelerator housing 10, gantry 20 and power/RF unit 30 and/or interfaces for receiving instructions. Such instructions may include an instruction to uncouple housing 10 from gantry 20. Output device 502 may also present images acquired by imaging device 40 to verify patient positioning prior to radiation treatment. Input device 501 and output device 502 are coupled to processor 503 and storage 504.

Operator console 50 may be in a room other than treatment room 1, in order to protect its operator from radiation. For example, treatment room 1 may be heavily shielded, such as a concrete vault, to shield the operator from radiation generated by the accelerator waveguide of housing 10.

Each of the devices shown in FIG. 1 may include less or more elements than those shown. In addition, embodiments are not limited to the devices shown in FIG. 1.

Figure 2A:
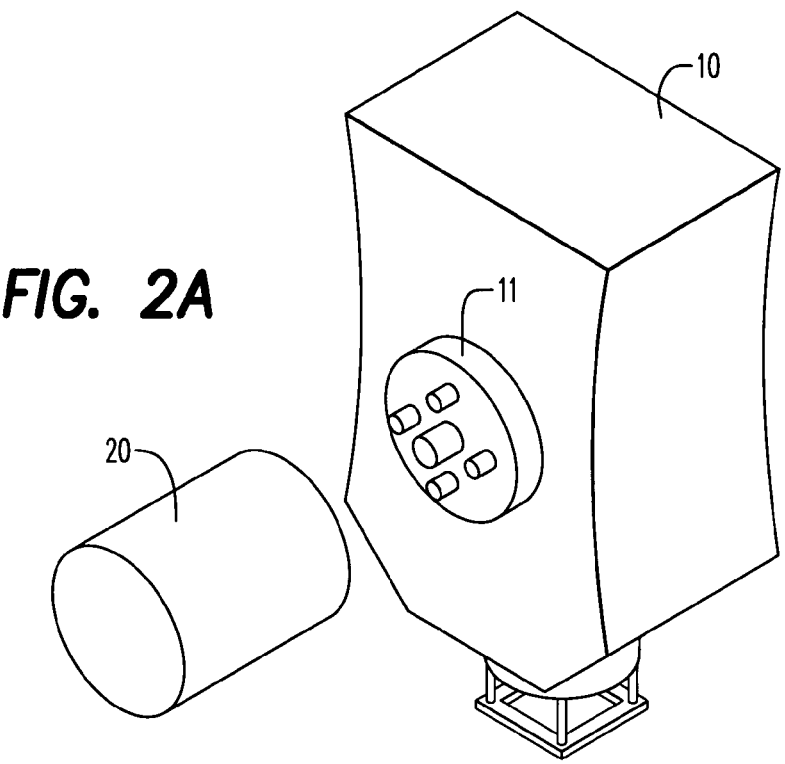
FIGS. 2A and 2B are perspective views of a linear accelerator housing according to some embodiments.

FIG. 2A is a perspective view of housing 10 according to some embodiments. Housing 10 includes interface 11 to couple housing 10 to a movable support such as gantry 20. As will be described below, such a movable support is not limited to a rotatable gantry, but may also include a multi-jointed robotic arm or other movable support.

Interface 11 may comprise any suitable arrangement to physically support housing 10 upon a movable support. Interface 11 may also or alternatively comprise any suitable structure to receive and/or emit any signals, power or fluid necessary for operating an accelerator waveguide housed therein. In some embodiments, interface 11 comprises bayonet mounting connectors.

Interface 11 need not comprise homogenous connectors located on one contiguous portion of housing 10 as pictured. According to some embodiments, the interface of housing 10 includes a mounting bracket to physically mount to a movable support, one or more discrete electrical connectors to receive various voltages, and two fluid couplings to transfer cooling fluid, any of which may be located on any suitable portion of housing 10.

Figure 2B:
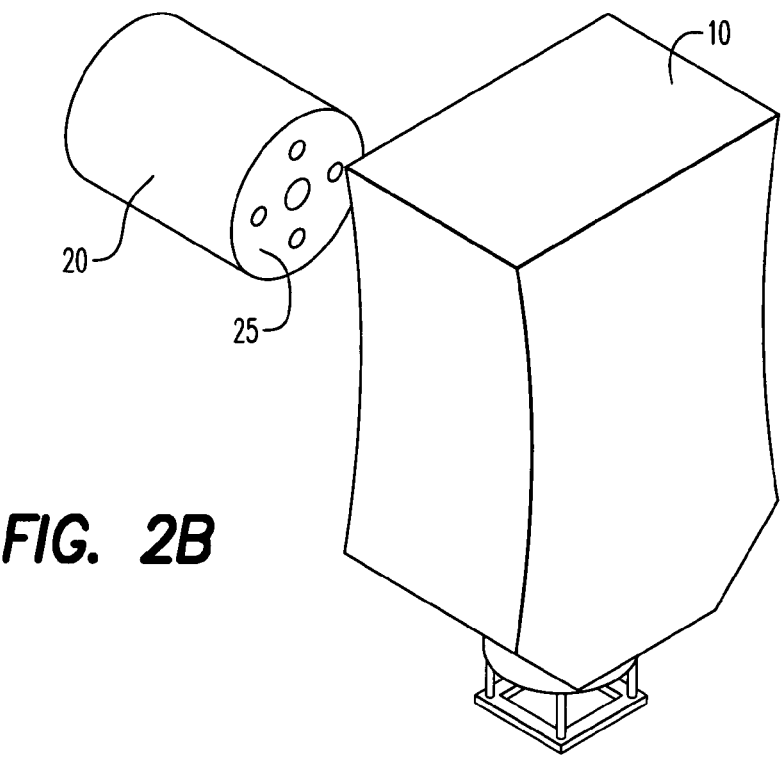

FIG. 2B is a perspective view of interface 25 of gantry 20. Interface 25 may be coupled to or uncoupled from interface 11 of housing 10. Accordingly, a design of interface 25 depends upon corresponding elements of interface 11. As mentioned with respect to interface 11, interface 25 may include heterogeneous mounting surfaces, connectors and couplings located anywhere on gantry 20.

Figure 3:
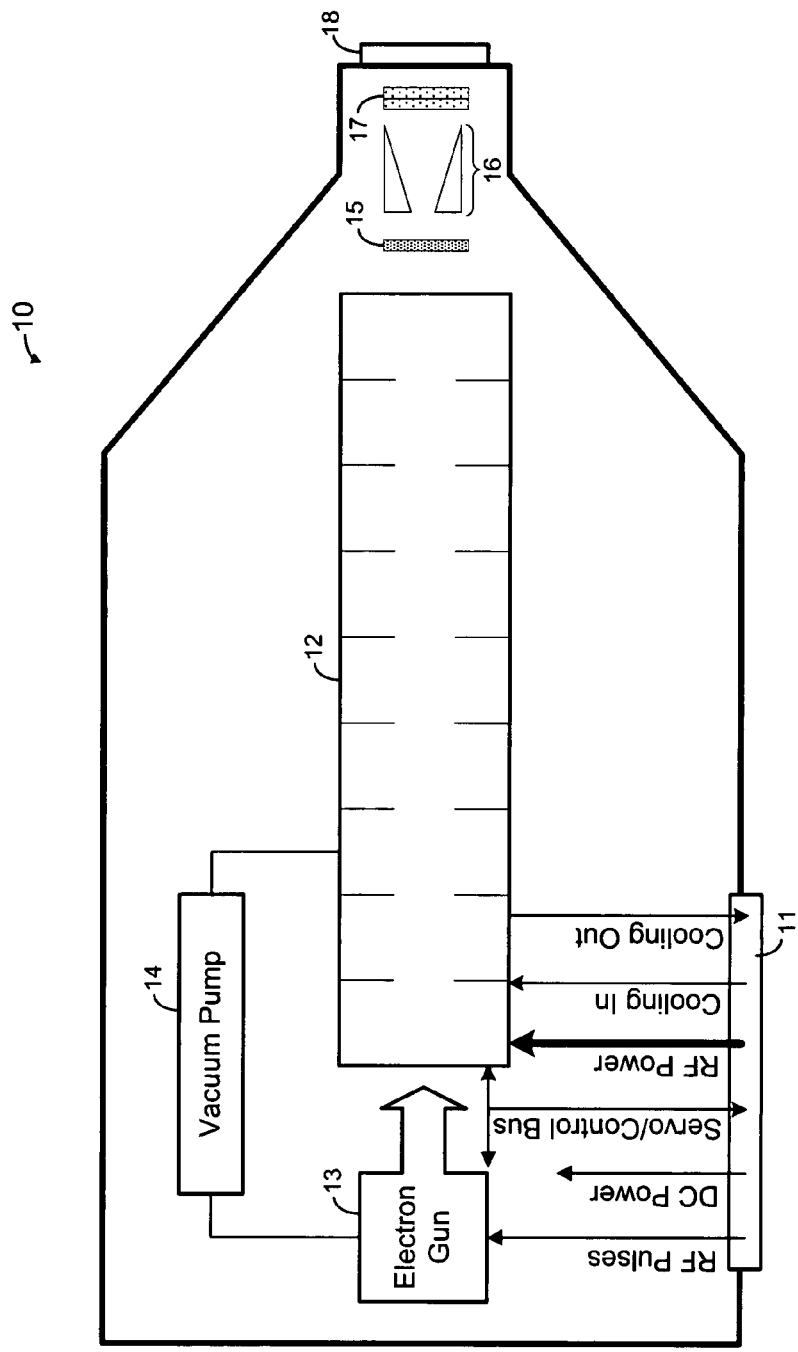
FIG. 3 is a block diagram of a linear accelerator system according to some embodiments.
Figure 4:
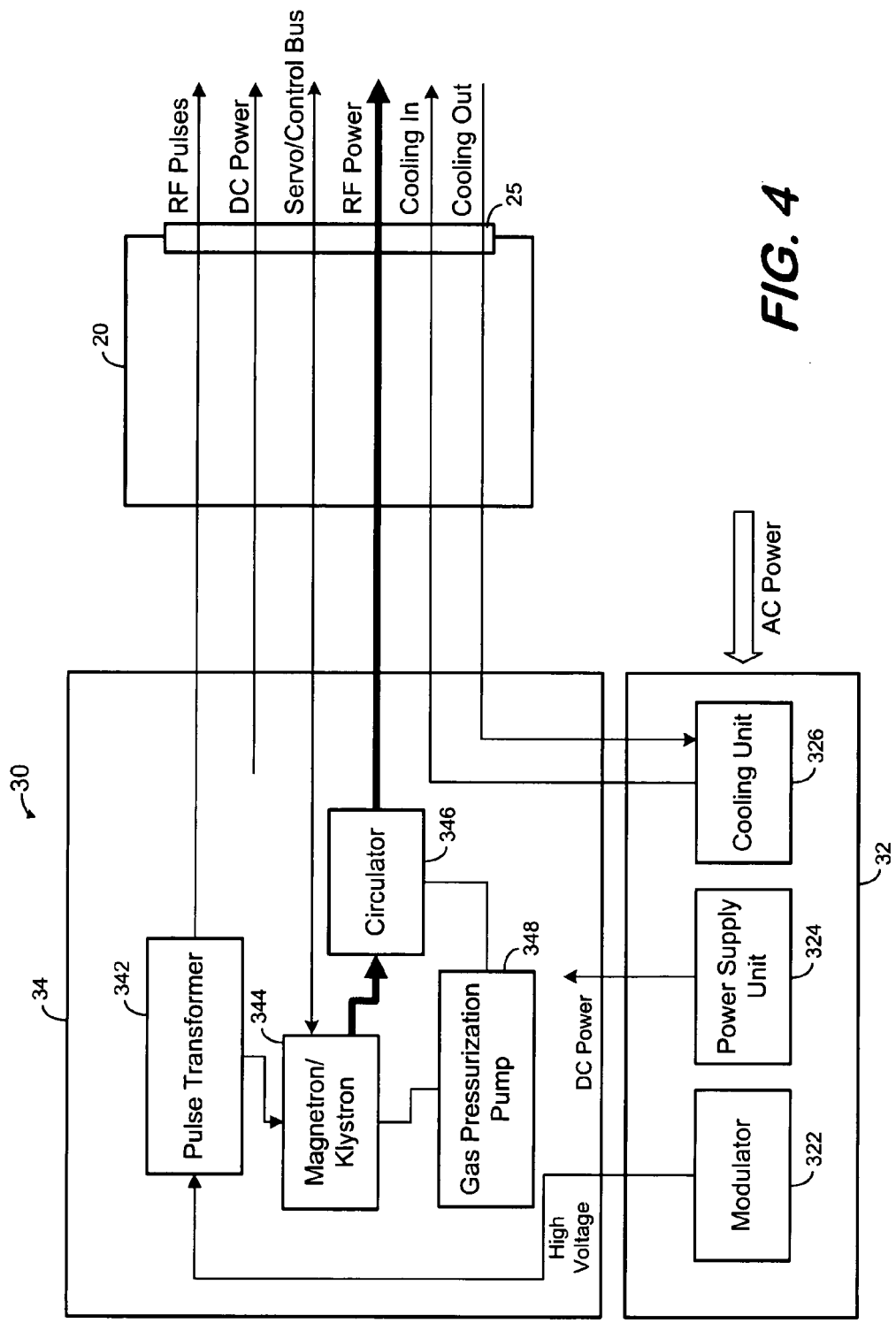
FIG. 4 is a block diagram of a power source, RF unit and a movable support according to some embodiments.

FIG. 3 is a block diagram of showing internal elements of housing 10 according to some embodiments. FIG. 4 shows corresponding internal elements of gantry 20 and power/RF unit 30 that may be suitable for use with the FIG. 3 embodiment of housing 10. The depiction of internal device elements in block diagram form is not intended to indicate relative sizes or spatial relationships of the elements, although some embodiments may be thus reflected.

Linear accelerator housing 10 of FIG. 3 includes interface 11 as described above, accelerator waveguide 12, electron gun 13, vacuum pump 14, target 15, collimator 16, dosimeter 17, and attachment bracket 18. Housing 10 may be lined with magnetic and radiation shielding material to isolate the elements therein.

Accelerator waveguide 12 may comprise any suitable accelerator waveguide design that is or becomes known. Generally, waveguide 12 includes cavities that are designed and fabricated so that electric currents flowing on their surfaces generate electric fields that are suitable to accelerate received electrons. The oscillation of these electric fields within each cavity is delayed with respect to an upstream cavity so that an electron is further accelerated as it arrives at each cavity.

Accelerator waveguide 12 receives the aforementioned electrons from electron gun 13. Electron gun 13 may comprise a heater, a cathode (thermionic or other type), a control grid (or diode gun), a focus electrode, an anode, and other elements. Electron gun 13, as shown, is driven by RF pulses received from interface 11.

The oscillating electric fields within the cavities of accelerator waveguide 12 are produced in part by an oscillating electromagnetic RF power wave received from interface 11. Accordingly, housing 10 may comprise an RF waveguide (e.g, denoted by a thick arrow in FIG. 3) to carry such a wave from interface 11 to waveguide 12.

Vacuum pump 14 maintains any necessary vacuum within waveguide 12 and electron gun 13. Vacuum pump 14, as well as any other elements of housing 10, may be powered using DC power received over interface 11. Cooling fluid conduits run between interface 11 and accelerator waveguide 12 for cooling waveguide 12 according to known techniques. Interface 11 also passes a servo/control bus to transfer control signals, including servo feedback signals for controlling the RF power delivered to housing 10.

Target 15 may comprise a hi-Z (i.e., high atomic weight) material such as Gold, Tungsten, or another suitable material. Upon receiving an accelerated electron beam from waveguide 12, such a target may generate a beam of photons having an energy spectrum suitable for radiation treatment. Collimator 16 shapes the photon beam according to signals receive via the servo/control bus of housing 10.

Dosimeter 17 may comprise any system for determining a radiation dose. Dose information acquired by dosimeter 17 may be used to control other elements of housing 10. The dose information may be transmitted to operator console 50 through interface 11 and console 50 may control other elements of treatment room 1 based thereon.

Bracket 18 may provide electrical and/or mechanical interconnects for desired accessory devices. For example, a secondary collimator may be mounted to housing 10 using bracket 18. Other possible devices include filters (e.g., flattening filters), shield blocks, and accessory trays.

FIG. 4 shows interface 25 of gantry 20 which may be coupled to and uncoupled from interface 11 of housing 10 according to some embodiments. As shown, each of the components passed by interface 25 originates and/or terminates at power/RF unit 30. Embodiments are not limited to this arrangement, in that one or more components passed by interface 25 may be provided by an element of gantry 20. For example, gantry 20 may comprise a power supply unit to provide DC power to housing 10 via interface 25.

Power/RF unit 30 of the FIG. 4 embodiment includes power unit 32 and RF unit 34. As shown, power unit 32 receives AC power from an external source such as a building's main power lines. Power unit 32 includes modulator 322 for generating high voltage power and power supply unit 324 for generating desired DC power. Power supply unit 324 may generate DC power of several different voltages and currents depending upon the needs of RF unit 34 and housing 10.

Cooling unit 326 may transmit cooling fluid to gantry 20, receive heated fluid from gantry 20, and cool the heated fluid before providing it again to gantry 20. Cooling unit 326 may include a pump, a compressor and any other suitable elements. Although the fluid is shown as passing through RF unit 34 between power unit 32 and gantry 20, in some embodiments cooling unit 326 is directly connected to gantry 20. Alternatively, in other embodiments, cooling unit 326 is directly connected to housing 10 and interface 25 does not pass any cooling fluid.

RF unit 34 includes pulse transformer 342 for generating high voltage RF pulses based on lower voltage power received from modulator 322. The RF pulses are transmitted to gantry 20 and on to housing 10 through interface 25 as shown. Pulse transformer 342 also transmits RF pulses to magnetron/klystron 344 according to some embodiments.

As shown, RF power generated by magnetron/klystron 344 is transmitted to circulator 346 by a first waveguide, and is transmitted from circulator 346 to interface 25 of gantry 20 via second waveguide. Gas pressurization pump 348 provides needed pressurization to both magnetron/klystron 344 and circulator 346. Any of the elements of RF unit 34 may be powered by DC power received from power supply unit 324.

Either a magnetron or a klystron may be used to generate RF power according to some embodiments. Circulator 346 is also optional in some embodiments. Some embodiments may employ an articulated waveguide such as that disclosed in U.S. Pat. No. 4,647,884, but embodiments are not limited thereto. Such articulated waveguides allow the magnetron and/or klystron and/or circulator to be placed outside the housing that contains the accelerating waveguide. In some embodiments, the magnetron and/or klystron and/or circulator are housed within the isocentric gantry, as it typical of treatment delivery machines with isocentric geometry.

Figure 5:
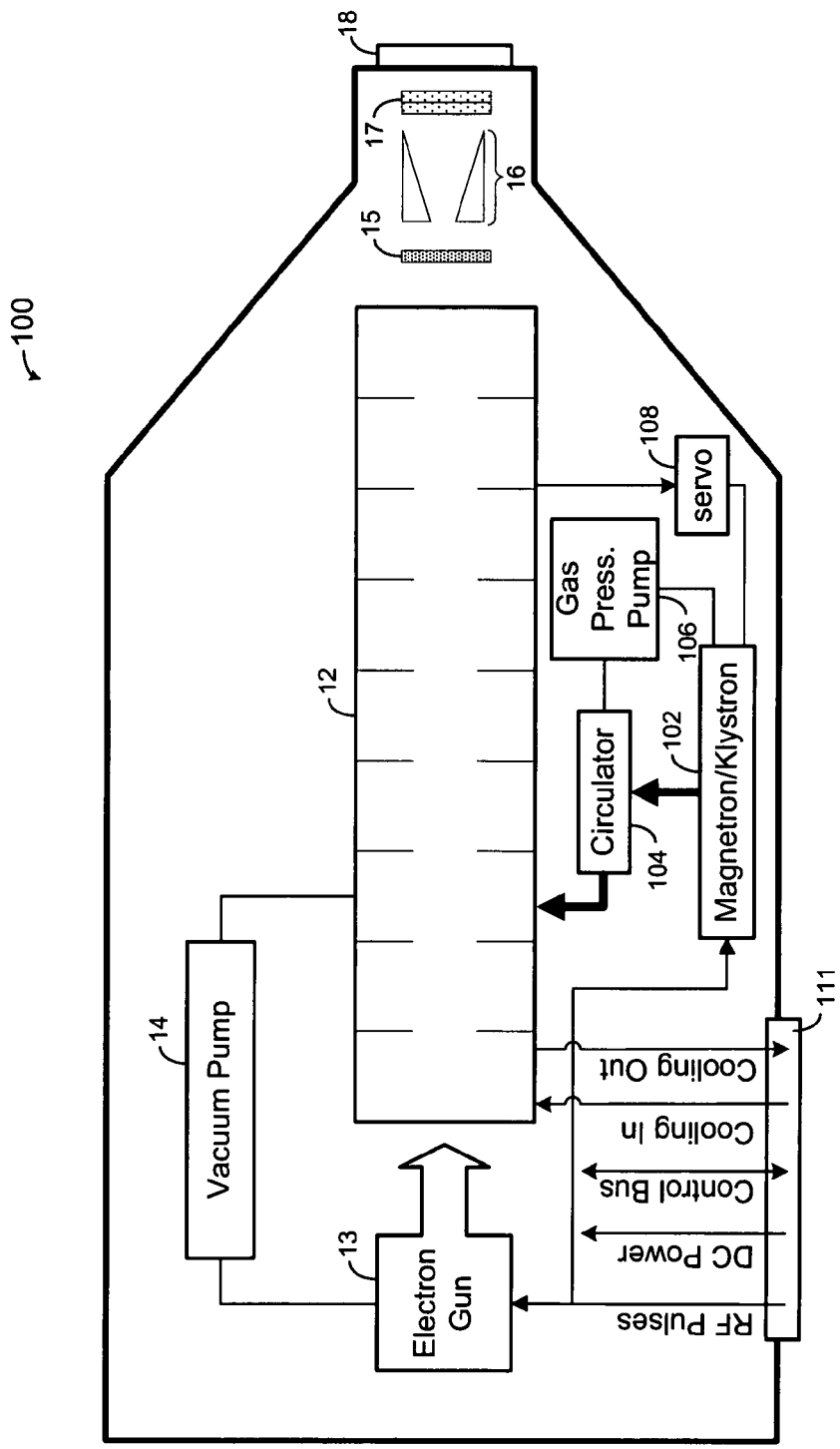
FIG. 5 is a block diagram of a linear accelerator system according to some embodiments.

FIG. 5 is an internal block diagram of housing 100 according to some embodiments. The operation and composition of the elements of housing 100 may be similar to that described with respect to the identically-numbered elements of FIG. 3. However, in contrast to housing 10, housing 100 includes magnetron/klystron 102, circulator 104, gas pressurization pump 106 and servo 108.

Magnetron/klystron 102 receives RF pulses to via interface 111 according to some embodiments. As described with respect to FIG. 4, magnetron/klystron 102 generates RF power based on the received RF pulses and transmits the RF power to circulator 104 by a first waveguide. Circulator 104 (optional), in turn, transmits the RF power to accelerator waveguide 12. Gas pressurization pump 106 provides pressurization to magnetron/klystron 102 and circulator 104, and servo 108 controls magnetron/klystron 102 based on signals received from accelerator waveguide 12.

Embodiments of housing 100 may advantageously avoid having to transmit RF power between housing 100 and a movable support to which housing 100 is coupled. In this regard, FIG. 6 illustrates movable support 200 and power/RF unit 300 that may be used in conjunction with housing 100 according to some embodiments.

Movable support 200 may comprise gantry 20, a multi-jointed robotic arm, or any other suitable support. Movable support 200 comprises interface 250 for coupling to interface 111 of housing 100. Interfaces 111 and 250 may comprise any suitable permutations of interfaces discussed herein or otherwise known.

Figure 6:
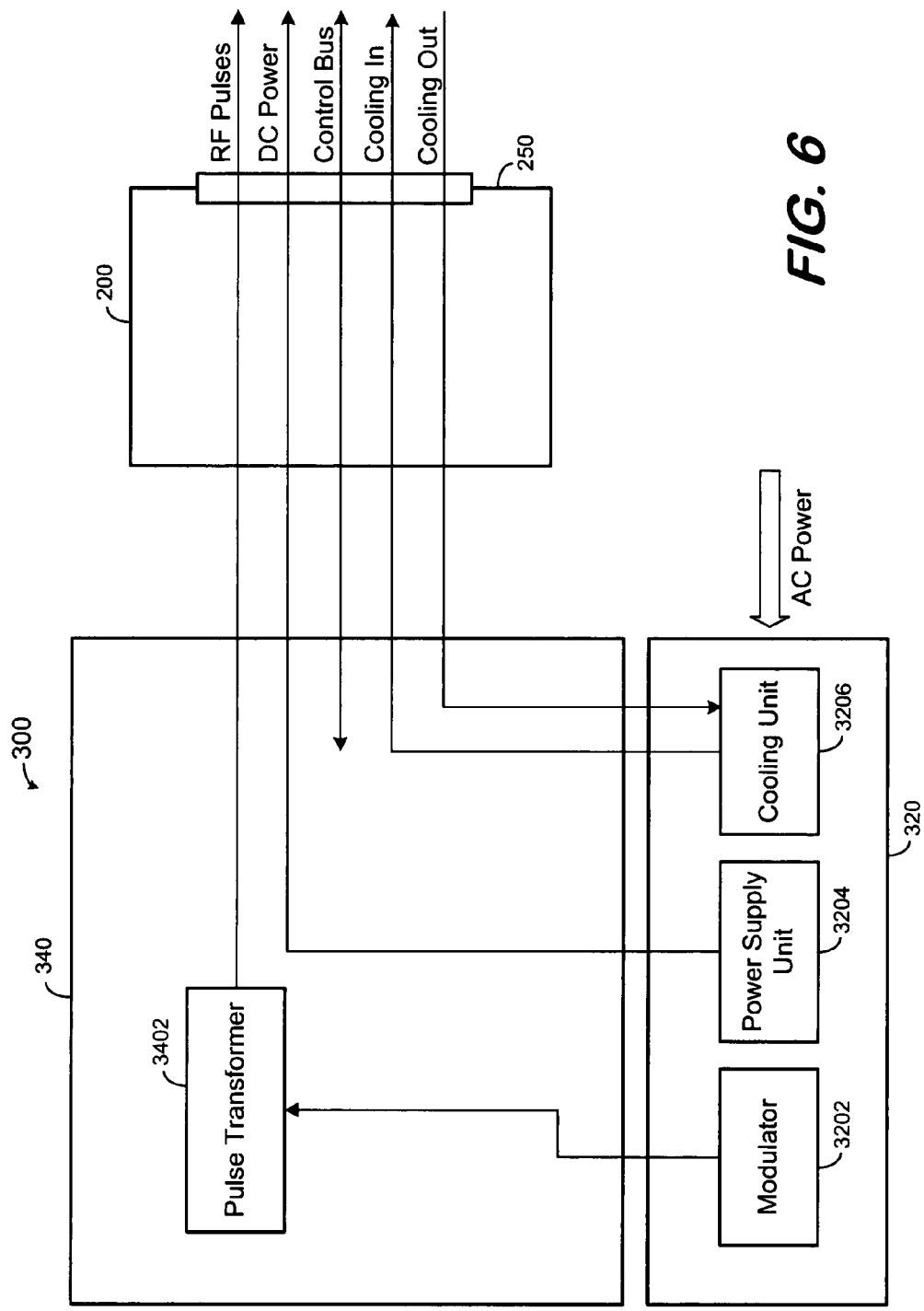
FIG. 6 is a block diagram of a power source, RF unit and a movable support according to some embodiments.

Power unit 320 of FIG. 6 is similar to power unit 32 of FIG. 4. Specifically, power unit 320 receives AC power from an external source and includes modulator 3202, power supply unit 3204 and cooling unit 3205. Modulator 3202 generates high voltage power for pulse transformer 3402 of RF unit 340. Power supply unit 3204 may various types of DC power depending upon the needs of RF unit 340 and housing 100. Cooling unit 3206 may transmit cooling fluid to and receive cooling fluid from gantry 200 through RF unit 340. As mentioned above, cooling unit 3206 may be directly connected to gantry 200 or to housing 100.

Figure 7:
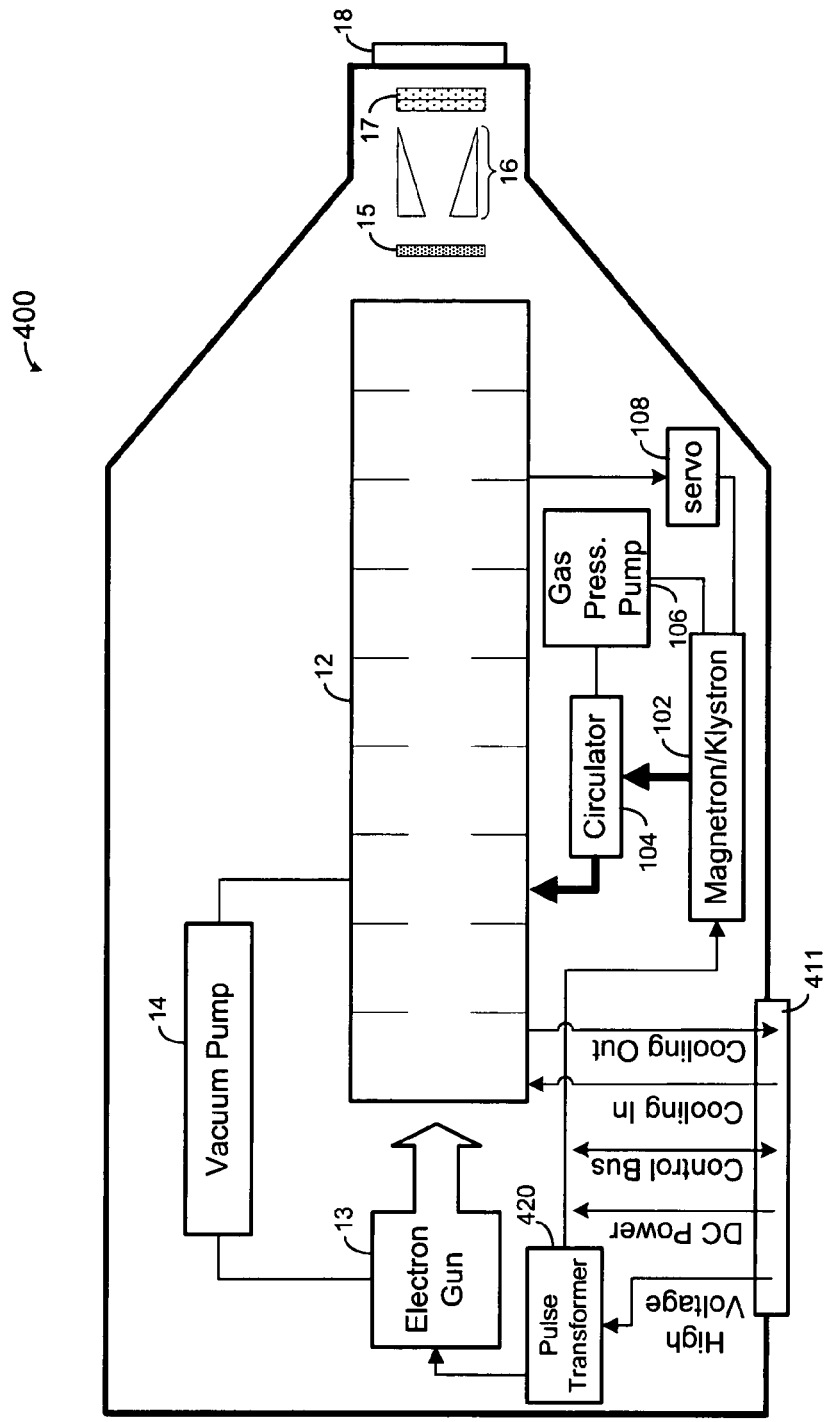
FIG. 7 is a block diagram of a linear accelerator system according to some embodiments.

FIG. 7 is an internal block diagram of housing 400 according to some embodiments. The operation and composition of the elements of housing 400 may be similar to that described with respect to the identically-numbered elements of FIGS. 3 and 5.

Rather than receive RF pulses from an external source, housing 400 includes pulse transformer 420 to receive a high voltage and generate RF pulses therefrom. The RF pulses are transmitted to electron gun 13 and magnetron/klystron 102 and used as described above. Interface 411 therefore differs from interface 111 by passing a high voltage signal instead of RF pulses. Embodiments such as housing 400 may advantageously eliminate the need for an RF unit locates proximate to housing 400.

Figure 8:
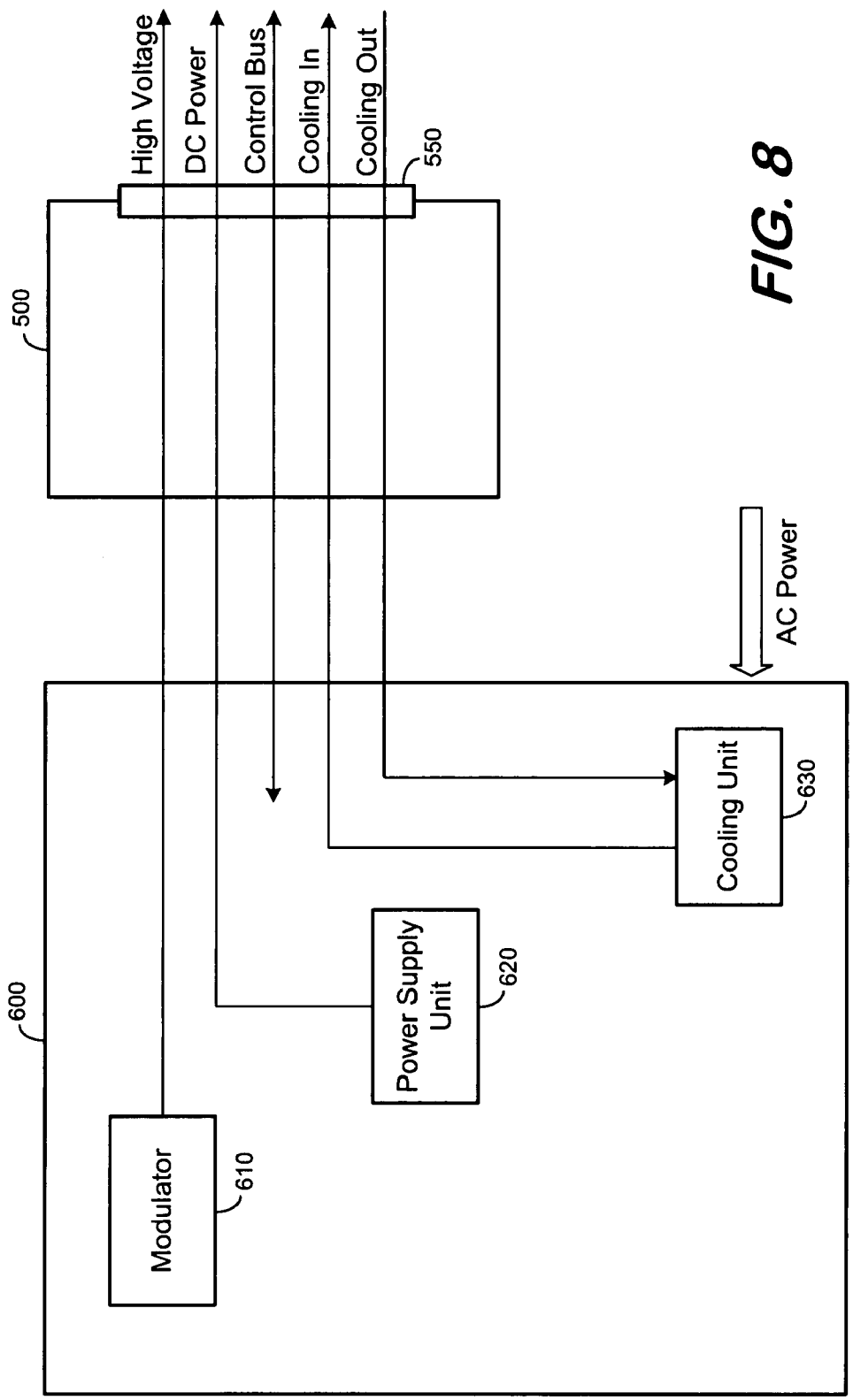
FIG. 8 is a block diagram of a power source, RF unit and a movable support according to some embodiments.

FIG. 8 illustrates movable support 500 and power unit 600 that may be used in conjunction with housing 400 according to some embodiments. Movable support 500 may comprise any other suitable support, including but not limited to gantry 20 or a multi-jointed robotic arm. Movable support 500 comprises interface 550 for coupling to interface 411 of housing 400. Interfaces 411 and 550 may comprise any suitable permutations of interfaces discussed herein or otherwise known.

Power unit 600 includes modulator 610 to supply high voltage power to housing 400 via interface 550. Also included are power supply unit 620 to provide DC power to elements of housing 400 and cooling unit 630 to transmit cooling fluid to and receive cooling fluid from housing 400 through support 500. Any number of integrated or separate cables, conduits, etc. may be used to connect the illustrated signals and fluids between support 500 and power unit 600.

Some embodiments may facilitate the selective use of two or more different movable supports with a single housing. An interface of the housing may be coupled to an interface of a first movable support as described therein, and the interface may then be uncoupled from the first support and coupled to an interface of a second support. Each support may be associated with a dedicated RF/power unit as described herein, or may be selectively connected to an appropriate RF/power unit when coupled to the housing. The latter arrangement may avoid duplication of both the housing elements and the elements of the RF power unit while providing two types of radiation treatment (e.g., isocentric and non-isocentric).

Figure 9:
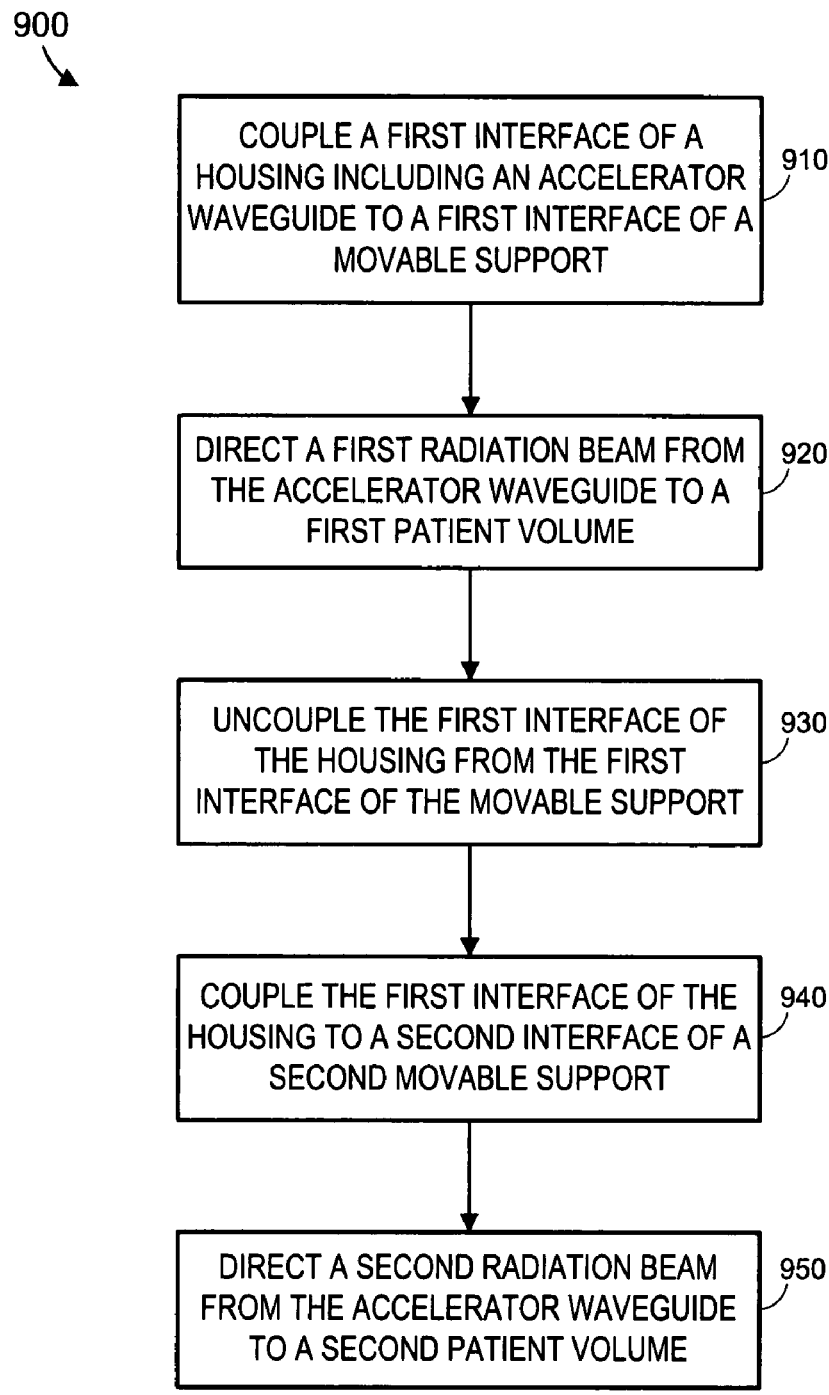
FIG. 9 is a flow diagram of process steps pursuant to some embodiments.

FIG. 9 is a flow diagram of a process according to some embodiments. Process 900 may be executed during a single radiation treatment or over the course of two different radiation treatments that involve the same or different patients. Process 900 may be performed using any suitable combination of hardware, software or manual means.

Some or all of process 900 may be performed in response to signals received from operator console 50. Such control may include transmission of a set of instructions and/or parameters associated with a radiation treatment plan to RF/power unit 30.

Figure 10:
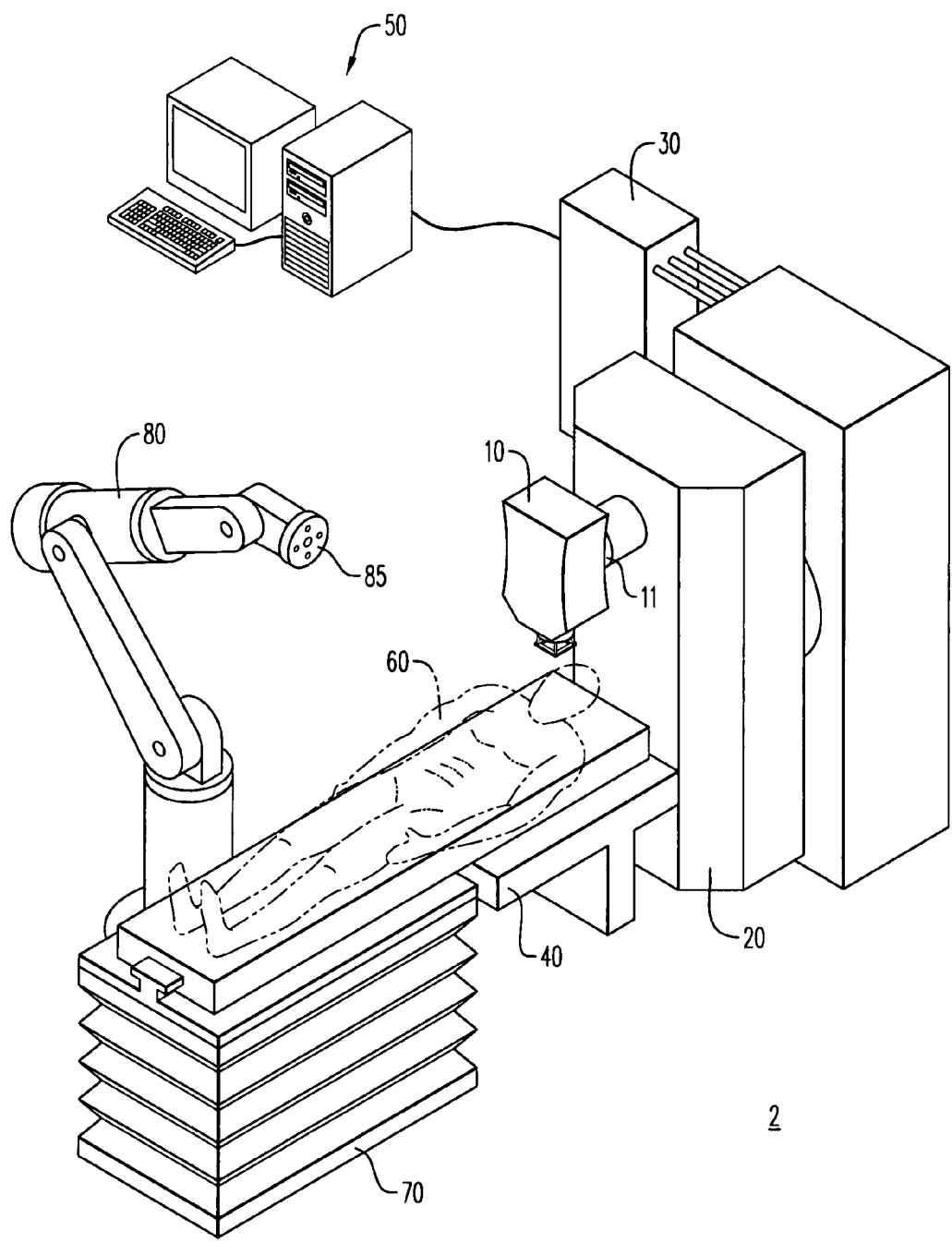
FIG. 10 is a perspective view of a treatment room according to some embodiments.

Initially, at 910, a first interface of a housing including an accelerator waveguide is coupled to a first interface of a movable support. FIG. 10 illustrates treatment room 2 after 910 according to some embodiments. Treatment room 2 includes housing 10, gantry 20 and power/RF unit 30 as described above. A first interface of housing 10 is coupled to an interface (not shown) of gantry 20.

Interface 11 may be coupled to the interface of gantry 20 by lifting housing 10 into the illustrated position using a device intended for this or other purposes, and/or manually. Coupling the interfaces at 910 may also include securing any clamps, connectors or other elements used to secure each portion of interface 11 to the interface of gantry 20.

A first radiation beam is directed from the accelerator waveguide to a first patient volume at 920. According to some embodiments, linear accelerator 12 of housing 10 is controlled to generate and emit a radiation beam toward an isocenter of patient 60. The radiation beam may exhibit an energy and dose rate specified by a radiation treatment plan.

After completion of 920, the first interface of the housing is uncoupled from the first interface of the first movable support. The uncoupling may comprise any steps used to couple the interfaces performed in reverse. The first interface of the housing is then coupled to a second interface of a second movable support.

FIG. 10 illustrates multi-jointed robotic arm 80 and interface 85 to which interface 11 may be coupled at 940. Multi-jointed robotic arm may comprise any suitable movable support, including but not limited a robotic arm such as that used in the Cyberknife® by Accuray®. Interface 11 may be coupled to interface 85 as described above with respect to 910. In some embodiments, housing 10 may be coupled to a support that is configured for movement within treatment room 2 and/or between treatment rooms or repair areas.

According to some embodiments, housing 10 includes a second interface for receiving signals and material needed for operation of accelerator waveguide 12. Interface 85 may be coupled to the second interface of housing 10 and housing 10 may then be moved away from gantry 20 at 940. Robotic arm 80 is therefore used to physically move housing 10 between gantry 20 and arm 80. The second interface of housing 10 need not be identical to interface 11 in such embodiments, and, if not identical, interface 85 may be different from the interface of gantry 20.

Figure 11:
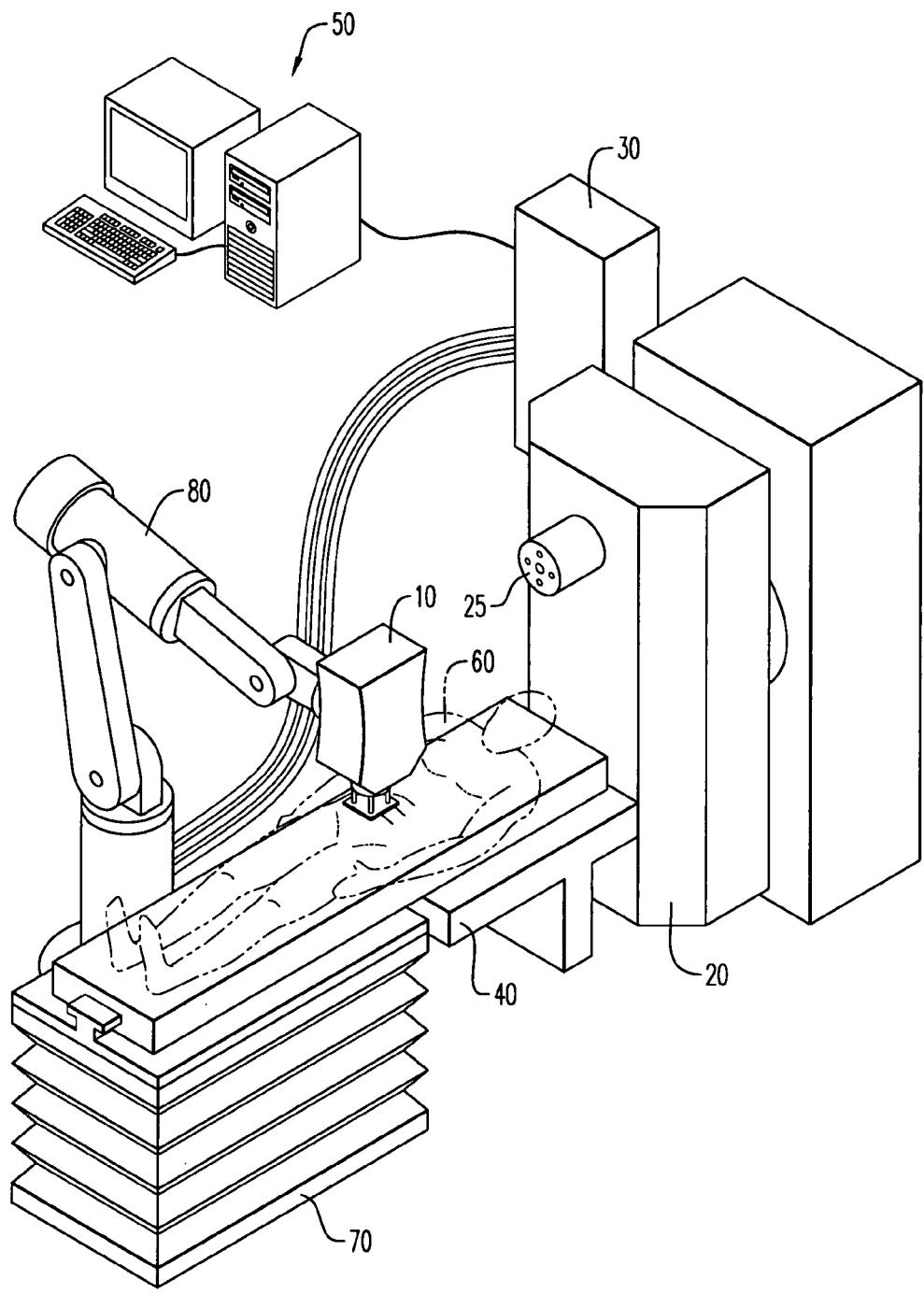
FIG. 11 is a perspective view of a treatment room according to some embodiments.

FIG. 11 illustrates treatment room 2 after 940 according to some embodiments. As shown, housing 10 is coupled to robotic arm 80. Also, RF/power unit 30 is connected to robotic arm 80 to provide signals, power and material thereto. In some embodiments, a dedicated unit provides power, signals and/or material to robotic arm 80 so that RF/power unit 30 need not be used in conjunction with both robotic arm 80 and gantry 20. Robotic arm 80 and/or gantry 20 may include such a dedicated unit according to some embodiments.

A second radiation beam is directed from the accelerator waveguide to a second patient volume at 950. Operator console 50 controls robotic arm 80 in some embodiments of 950 to move housing 10 to a specified location and also controls accelerator waveguide 12 to generate the second radiation beam. In the illustrated scenario, the second radiation beam is directed to an abdominal volume of patient 60.

The first movable support and the second movable support of process 900 are not limited to the positions shown FIGS. 10 and 11. For example, gantry 20 may be disposed at any rotational angle while the first radiation beam is directed to the first patient volume at 920. Moreover, 920 may comprise successive radiation beams delivered from different rotational angles of gantry 20. Similarly, 950 may include direction of radiation beams from housing 10 while robotic arm 80 is disposed in different respective positions.

Some embodiments provide two or more housings including respective accelerator waveguides. Each of the two or more housings may be particularly suited to the use of specific beam energies, dose rates or collimation methods, and/or two or more of the housings may be identical. Some embodiments may provide increased machine uptime by facilitating rapid replacement of a malfunctioning housing. Although radiation treatment units are conventionally calibrated or commissioned at the site of treatment delivery, it may be beneficial to calibrate or commission systems according to some embodiments at a factory or other site.

The several embodiments described herein are solely for the purpose of illustration. Therefore, persons in the art will recognize from this description that other embodiments may be practiced with various modifications and alterations.

What is claimed is:

1. An apparatus comprising:
    an accelerator waveguide to generate an accelerated radiation beam;
    a housing to house the accelerator waveguide, the housing comprising an interface to couple the housing to and to decouple the housing from a movable support; and
    an electron gun disposed within the housing, the electron gun to receive signals from the movable support through the interface and to inject electrons into the accelerator waveguide based on the signals, wherein the interface is to receive RF power, and wherein the RF power is transmitted to the accelerator waveguide, wherein the movable support comprising a gantry to rotate about a patient isocenter and a second interface to mate with the interface.

2. An apparatus according to claim 1, further comprising:
    a RF power generator disposed in the housing,
    wherein the RF power is transmitted to the accelerator waveguide.

3. An apparatus according to claim 1, wherein the interface is to receive cooling fluid.

4. An apparatus according to claim 1, the housing further comprising:
    a second interface to couple the housing to and to decouple the housing from a second movable support.

5. An apparatus according to claim 1, further comprising:
    the movable support, the movable support comprising a multi-jointed robotic arm and a second interface to mate with the interface.

6. An apparatus comprising:
    a movable support comprising an interface to selectively receive and decouple a housing including an accelerator waveguide and an electron gun, wherein the interface is to provide signals from the movable support through the interface to the housing to control the electron gun in the housing based on the signals, wherein the interface is to provide RF power to the accelerator waveguide and wherein the moveable support comprising a gantry to rotate about a patient isocenter.

7. An apparatus according to claim 6,
    wherein the interface is to provide cooling fluid to the accelerator waveguide.

8. An apparatus according to claim 6, the movable support comprising a multi-jointed robotic arm.

9. A method comprising:
    coupling a first interface of a housing to a first interface of a movable support, the housing comprising an accelerator waveguide to generate an accelerated radiation beam;
    uncoupling the first interface of the housing from the first interface of the movable support;
    providing first signals from the first interface of the movable support to an electron gun disposed within the housing, the electron gun to inject electrons into the accelerator waveguide to generate a first radiation beam based on the first signals;
    coupling a second interface of the housing to a second interface of a second movable support; and
    providing second signals from the second interface of the second movable support to the electron gun, the electron gun to inject electrons into the accelerator waveguide to generate a second radiation beam based on the signals.

10. A method according to claim 9, further comprising:
    providing cooling fluid from the first interface of the movable support to the accelerator waveguide.

11. A method according to claim 9, further comprising:
    providing RF power from the first interface of the movable support to the accelerator waveguide.

12. A method according to claim 9, wherein the movable support comprises a rotatable gantry, and
    wherein the second movable support comprises a multi-jointed robotic arm.

13. A method according to claim 9, wherein the first radiation beam is directed to a patient isocenter, and
    wherein the second radiation beam is directed at a patient volume other than the patient isocenter.

* * * * *